United States Patent [19]

Kulkarni et al.

[11] Patent Number: 4,844,616

[45] Date of Patent: Jul. 4, 1989

[54] INTERFEROMETRIC DIMENSIONAL MEASUREMENT AND DEFECT DETECTION METHOD

[75] Inventors: Murlidhar V. Kulkarni; William H. Lancaster, Jr., both of Tucson, Ariz.

[73] Assignee: International Business Machines Corporation, Armonk, N.Y.

[21] Appl. No.: 200,262

[22] Filed: May 31, 1988

[51] Int. Cl.⁴ .............................................. G01B 9/02
[52] U.S. Cl. .................... 356/351; 356/358; 356/359; 356/237
[58] Field of Search ............... 356/351, 358, 359, 235

[56] References Cited

U.S. PATENT DOCUMENTS

| | | | |
|---|---|---|---|
| 4,280,766 | 7/1981 | Goss | 356/350 |
| 4,286,878 | 9/1981 | Pircher | 356/350 |
| 4,298,283 | 11/1981 | Makosch et al. | 356/351 |
| 4,358,201 | 11/1982 | Makosch | 356/351 |
| 4,552,457 | 11/1985 | Giallorenzi et al. | 356/345 |
| 4,652,744 | 3/1987 | Bowers et al. | 250/227 |
| 4,714,348 | 12/1987 | Makosch | 356/351 |

FOREIGN PATENT DOCUMENTS 0226658  1/1987  European Pat. Off. .

OTHER PUBLICATIONS

SPIE vol. 316 High Resolution Soft X-Ray Optics (1981) "Surface Profiling by Electro-Optical Phase Measurements", by G. Makosch et al. pp. 42–53.
Photographic Sciences Corporation, 1987, "MP2000 Non-Contact Surface Profiler".

Primary Examiner—Davis L. Willis
Assistant Examiner—Matthew W. Koren
Attorney, Agent, or Firm—Manny W. Schecter

[57] ABSTRACT

The invention is a method for detecting both surface topography and defect presence using an AC interferometer. Surface topography measurements are maximized by adjusting the signal voltage of the light modulator to a relative phase-sensitive value. Defect detection is maximized by adjusting the signal voltage of the light modulator to a relatively phase-insensitive value. This method not only allows for heretofore unknown defect detection by an AC interferometer but, because the signal voltage can be switched electronically, permits both observations to be taken at a high speed and for many points of a specimen, thereby making the method suitable for the manufacturing environment. More specifically, the method would be applicable to both optical disk and microchip manufacturing.

6 Claims, 2 Drawing Sheets

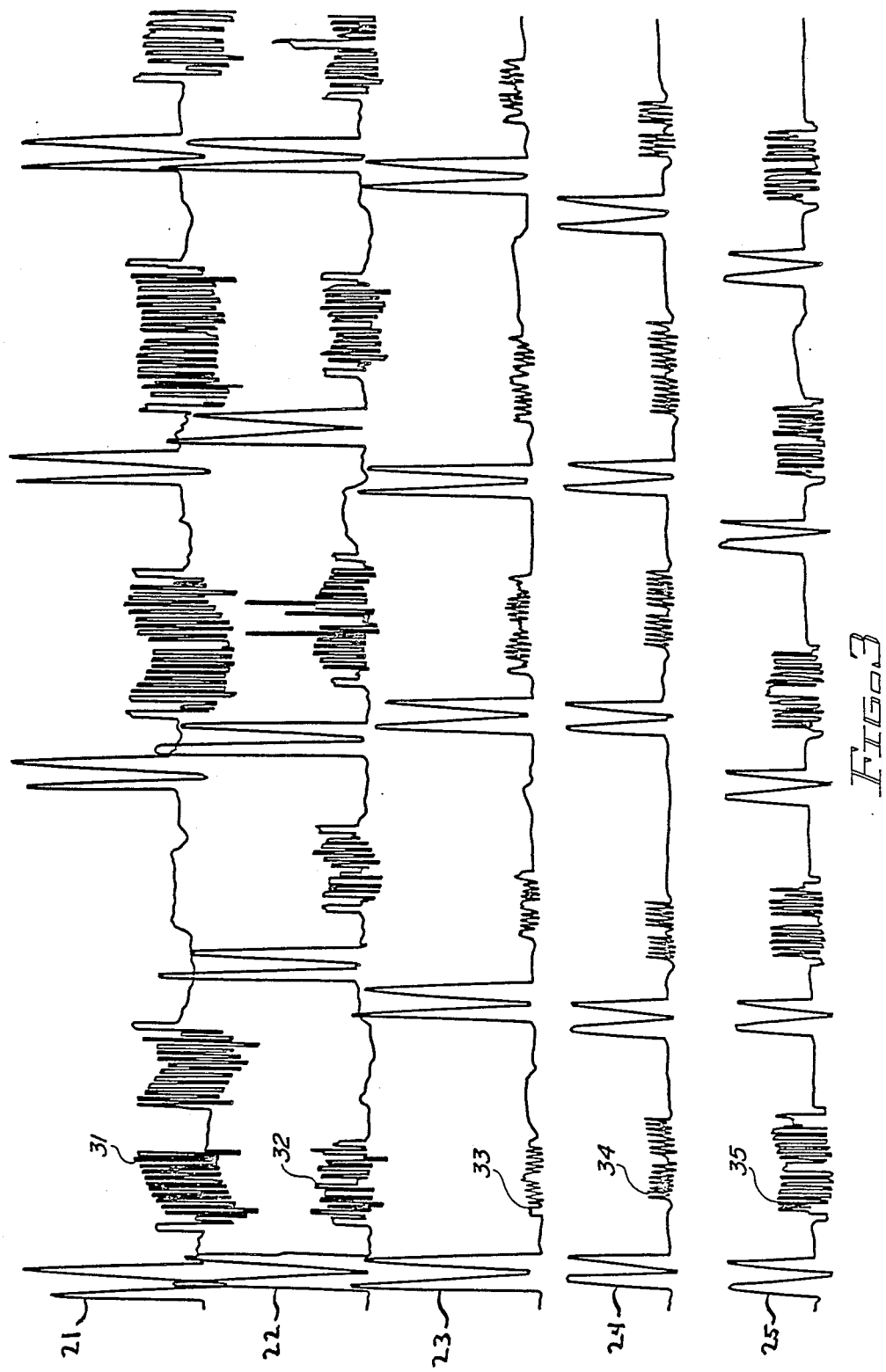

INTERFEROMETRIC DIMENSIONAL MEASUREMENT AND DEFECT DETECTION METHOD

BACKGROUND OF THE INVENTION

1. Field of the Invention

This invention relates to an interferometric method for dimensional measurements and defect detection. More particularly, the invention is a variable phase contrast interferometric method permitting dimensional measurements without complex computer calculation and also defect detection.

2. Description of the Related Art

In practically all fields of technology, the processing tolerances observed during the manufacture of parts have been tightened considerably. This trend has been most evident in the manufacture of integrated semiconductor circuits in the submicron range and for the manufacture of magnetic and optical storage disks, since the extreme miniaturization and increased packaging densities necessitate extremely plane and flawless surfaces. To meet these tightened processing tolerances, extremely accurate, high speed, and automatic measuring techniques are required for the control of materials, for the monitoring of production processes, and for final testing.

Past methods used for dimensional measurements include ellipsometric and stylus techniques. Ellipsometric methods use polarized radiation incident on the surface to be measured at a large angle, the ellipticity of which is measured after reflection at the surface measured. The necessary complicated mathematical calculations are so time consuming that it is not possible to examine a great number of measuring points on one sample for manufacturing control for final test during production. Stylus measurement techniques involve the running of a sensitive electromechanical stylus across a surface to be measured. However, the mechanical contact inherently required by this technique makes it impractical for use on the delicate surfaces of miniaturized semiconductor circuits or data recording disks.

A variety of interferometric techniques are also known for making dimensional measurements. In general, these techniques involve the observation of the interference pattern created by light beams reflecting off the surface being observed Some interferometric techniques include the use of light beams of at least two different wavelengths. Examples of multiple wavelength interferometric methods are shown in U.S. Pat. Nos. 4,652,744 and 4,552,457. Such multiple wavelength techniques suffer from the disadvantage that their measurements depend on the amount of light reflected from the observed surface, which is determined in part by the focal plane of each of the incident light beams thereon The flatness of the observed surface thus limits the applicability of such techniques for use in making dimensional measurements, such as step heights.

Amplitude shearing interferometry may also be used for making dimensional measurements. This technique employs two coherent light beams generated from the same source. To measure the step height on the surface of a specimen, for example, the two light beams are made to reflect from the specimen surface on different sides of the step. The step causes a difference in the path length of the two light beams. By observing the shift in the interference pattern of the two light beams caused by the step, the amount of the shift can be geometrically translated into the step height. Amplitude shearing techniques suffer from two disadvantages. First, such measurements can only be made where the step height does not exceed half the wavelength of the light used. This is because the amount of shift in the interference pattern for such step heights prevents the unequivocal location of the interference maxima and minima. Another disadvantage of amplitude shearing interferometry is that the measurement of small step heights is limited by one's ability to resolve the shift in the interference pattern. The resolution of the interference pattern shift is limited to approximately one-tenth of the wavelength of the light used because multiple light waves will actually be detected by the system photo detector.

Phase shearing interferometry is a technique with improved interference resolution compared with that of amplitude shearing interferometry. Phase shearing interferometry has been disclosed in U.S. Pat. No. 4,298,283 and a related publication. Makosch, G., Solf, B., "Surface profiling by electro-optical phase measurements", SPIE Vol. 316 High Resolution Soft X-Ray Optics (1981), pgs. 40–53. The technique uses a polarized light beam which is passed through an electro-optical phase modulator and resolved into two orthogonally polarized beams using beam splitting optics consisting of a Wollaston prism and a focusing lens, the two laser beams are focused on the object surface as colinear beams. The two beams reflect from the object surface on opposite sides of the step height therein. The reflected beams are combined by the Wollaston prism and are brought to interference passing through a polarizer preceding the photodetector. The step height may be calculated mathematically from the phase shift imparted between the two beams. The phase shift is itself calculated from the intensity of the beams measured by the photodetector. The light intensity measured at the photodetector varies sinusoidally with the voltage applied to the phase modulator. By measuring the detected intensity at three different voltages, the phase shift and hence the step height can be calculated without variations caused by reflectivity of the object surface This technique is an improvement over amplitude shearing interferometry in that resolution to approximately 1/300 of the wavelength of light used can be achieved. U.S. Pat. No. 4,358,201 and European Patent Application No. 0226658 also show phase shearing interferometers with some modification, such as the use of a Foucalt prism in place of the Wollaston prism.

Although phase shearing interferometry allows for improved resolution, the technique suffers from the disadvantage that three intensity measurements at different voltages, and the calculations associated therewith, result in slow processing times. The time required for measurements is such that the tool is not suitable for use in the manufacturing environment. The MP-2000 non-contact surface profiler tool, marketed by Photographic Sciences, Corp., uses a technique similar to phase shearing interferometry for measuring surface roughness in the manufacturing environment. The tool is similar to a phase shearing interferometer, except that no electro-optical phase modulator is used. Instead, a differential detector is used after the beam is deflected by a polarized beam splitter. However, because this tool only makes a single intensity measurement, variations in surface flatness and reflectivity at each point of reflection will affect the intensity detected. For this reason, the beams incident upon the object surface are brought extremely close together, thereby making the tool impractical for use in dimensional measurements such as for step height. Information on the MP-2000 tool was acquired from a 1987 product brochure, which lists the following address for contact to receive additional information: Photographic Sciences Corp., 770 Basket Road, P.O. Box 338, Webster, N.Y. 14580-0338.

Other interferometers are known in which the voltage applied to a light beam phase modulator is selected so as to maximize the resolution achievable by the system. For example, U.S. Pat. Nos. 4,286,878 and 4,280,766 disclose fiber optic interferometric gyrometers. These gyrometers sense rotation by measuring the difference in time it takes for light or other electro-magnetic waves to pass in opposite directions through a common path loop whose rotation is to be measured. If the two beams are only slightly out of phase, the light intensity at the detector will not vary significantly for small changes in phase difference between the two beams because the light intensity versus phase difference curve will be at a location of substantially zero slope. To resolve this problem, the references disclose the use of a phase difference imparted to the two light beams reaching the detector, such that the beams are 90 degrees out of phase at a zero rotation rate of the fiber optic loop. This assures that the system operates at a point on the light intensity versus phase difference curve wherein any slight change in phase difference between the beams of the pair results in a substantial change in the intensity of light falling on the detector (i.e. at or near the point of inflection of the curve). However, neither these or any of the aforementioned references, provide for both dimensional measurements and defect detection in the manufacturing environment.

SUMMARY OF THE INVENTION

In view of the foregoing, it is the principal object of this invention to improve methods for making dimensional measurements in the manufacturing environment.

Another object of this invention is a method for making dimensional measurements and the detection of defects in the manufacturing environment.

These and other objects of this invention are accomplished using phase shearing interferometry, and the observation that the intensity measurement at the photo detector is a sine wave type function of the phase difference between two orthogonally polarized beams. At or near the extrema in the intensity versus phase difference curve, the intensity does not change much with increasing or decreasing phase difference. The interferometer is therefore said to be operating in the "phase insensitive" mode, whereby the intensity measured by the photodetector is a function of the reflectivity of the surface being observed. Reflectivity of the surface is in turn a function of the presence of defects. At or near the points of inflection in the intensity versus phase difference curve, the intensity changes rapidly with increasing or decreasing phase difference. The interferometer is therefore said to be operating in the "phase sensitive" mode, thereby making dimensional measurements possible. Thus, by applying the appropriate voltage to the phase modulator, the interferometer may be made phase sensitive or phase insensitive. Since only a single measurement is taken in either mode, no complex computer calculations are required. Because the reflectivity information in the reflected beams can be minimized, the incident beams are not required to be extremely close together, making the technique suitable for dimensional measurements such as step height. In addition, because the voltage applied to the phase modulator can be switched at rapid electronic rates, both dimensional measurements and defect detection can be made on the fly using the same pull in the manufacturing environment.

The foregoing and other objects, features, and advantages of the invention will be apparent from the following more particular description of the preferred embodiment of the invention, as illustrated in the accompanying drawing.

BRIEF DESCRIPTION OF THE DRAWING

FIG. 3 shows plots of the intensity detected by the apparatus of FIG. 1 when the incident beams are scanned across the same series of parallel grooves in a disk.

DESCRIPTION OF THE PREFERRED EMBODIMENT

Figure 1:
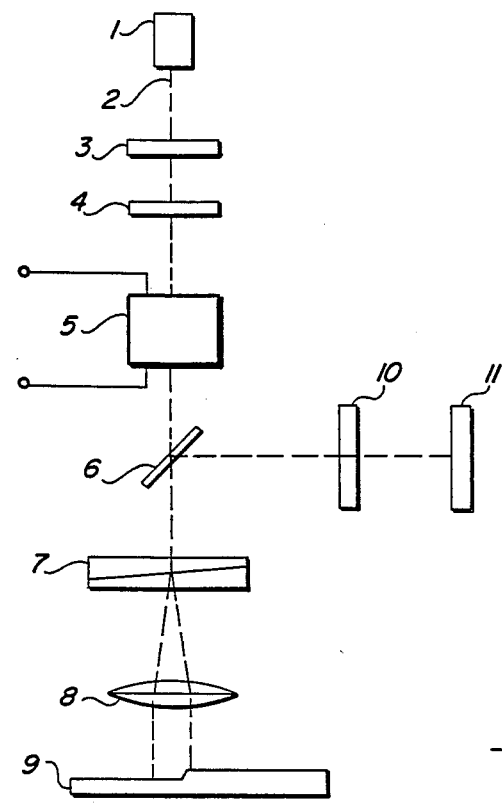
FIG. 1 shows a schematic diagram of an apparatus suitable for carrying out the invention.

Referring to FIG. 1, the principle optical arrangement for carrying out the invention and its operation will now be described.

Laser 1 generates a linearly polarized beam 2 which is suitably rotated by $\lambda/2$-plate 3 and polarized again by polarizer 4. Phase modulator 5 resolves the beam into two orthogonally polarized beams. The individual beams are polarized in the X and Y directions. One of the beams is phase shifted by the phase modulator which operates electrooptically or piezoelectrically. The amount of phase shift between the two beams is dependent on the voltage applied to the modulator.

The X and Y beams next pass through beam splitter 6 where they reach Wollaston prism 7. The Wollaston prism splits the X and Y beams apart as shown in the drawing. The angle of separation between the two beams varies according to the thickness of prism 7 and the slope of the interface of the components which comprise prism 7. The thus separated beams are then focused on the surface of object 9 by objective lens 8. The drawing shows a step height in object 9, which is located between the separated beams. However, the drawing could show a sloped object surface under the beams, or a defect existing on the surface of the object, such as particulate matter. The reflected beams are combined again upon passing through objective lens 8 and Wollaston prism 7. Upon partial reflection by beam splitter 6, the beams pass through polarizer 10 where they reach photodetector 11. In addition, the beams pass through a phase plate located on either side of polarizer 10, not shown in FIG. 1. Photodetector 11 senses the intensity of the light incident thereon.

The total amount of light reaching detector 11 is described by equation 1, wherein $J_1$ and $J_2$ are the intensities of the particular reflected beams, $\zeta$ is the inherent phase shift introduced by the interferometer, and $\zeta_m$ is the phase shift resulting from the difference in optical path length of the two beams.

$$J = J_1 + J_2 + 2\sqrt{J_1 J_2} \cos(\zeta - \zeta_m) \quad (1)$$

The intensity of each reflected beam is a function of its incident intensity and the surface reflectivity of the object. The phase difference $\zeta_m$ is a function of the surface topography, such as step heights or slopes, of the object between the points of incidence of the two beams. The phase difference $\zeta$ is a function of the optical components in the interferometer and the voltage applied to phase modulator 5. The optical components which affect $\zeta$ include Wollaston prism 7 and the direction of polarizer 10. Hence, the light intensity measured at the photodetector varies sinusoidally with the linear variance of the voltage applied to modulator 5. The sinusoidal curve has a characteristic phase shift $\zeta_m$. $\zeta_m$ is defined in equation 2, in which $\lambda$ is the wavelength of the laser and h is the optical path difference of the two reflected beams.

$$\zeta_m = \frac{4\pi h}{\lambda} \quad (2)$$

Thus, a geometrical step or slope in the surface of the object may be calculated by using the intensities detected at photodetector 11 and equations 1 and 2. By measuring the intensities at photodetector 11 at three different modulator voltages and applying complex mathematical analysis, the variance in intensities $J_1$ and $J_2$ caused by the difference in reflectivity across the surface of the object can be accounted for. For a further description of such analysis, one is referred to the article by Makosch and Solf cited earlier, hereby incorporated by reference.

The high efficiency dimensional measurement test of this invention operates to eliminate the need for intensity measurements at three different applied modulator voltages and the calculations associated therewith. Instead, a single measurement is made at the modulator voltage which maximizes sensitivity to the beam phase difference and minimizes sensitivity to the object surface reflectivity.

Figure 2:
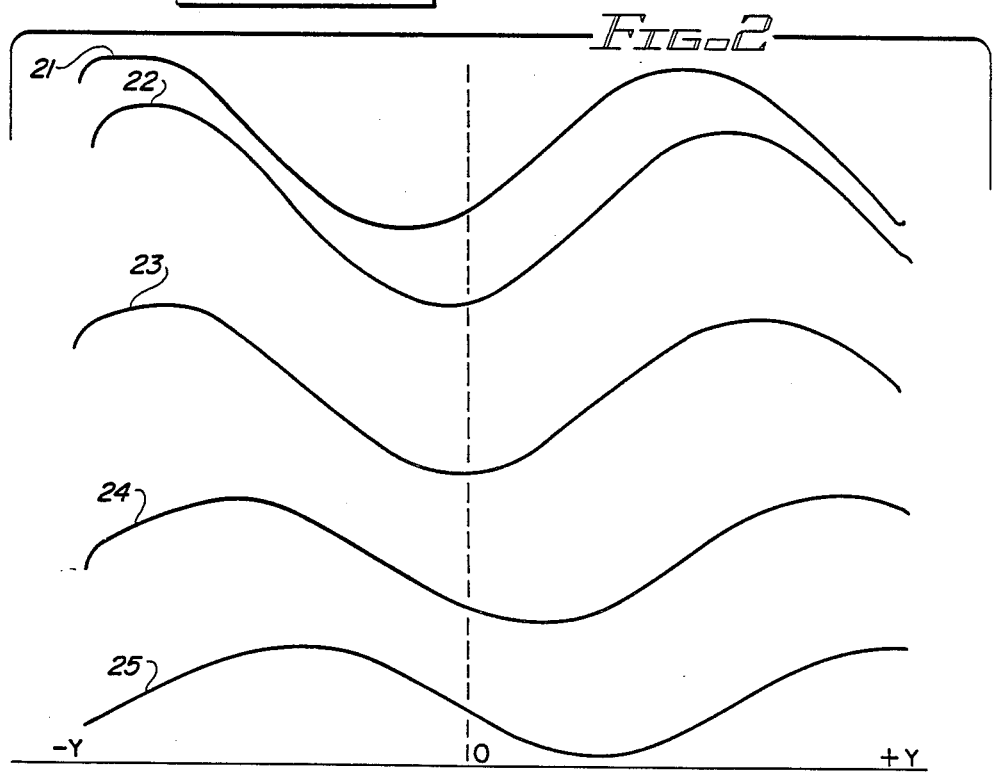
FIG. 2 shows a plot of the intensity detected by the apparatus of FIG. 1 as the voltage applied to the phase modulator is cycled from $-V$ to $+V$ volts.

FIG. 2 shows the sinusoidal variance of the intensity detected by photodetector 11 as the voltage applied to phase modulator 5 is cycled between an arbitrary $-v$ and $+v$ volts. The response of the intensity half-way along the curve represents the situation when no voltage is applied to modulator 5. Plots 21 through 25 were obtained by systematically rotating the phase plate in front of the detector, thereby introducing a phase shift between the two orthogonal beams. Thus, it can be seen that the point on the sinusoidal curve that the interferometer is operating at is a function of the rotation of phase plate 10. The extrema of the curves shown, having slopes approaching zero, indicate points on the curve in which the intensity detected is relatively insensitive to the voltage applied to modulator 5. The points of inflection of the curves shown, having slopes of relatively large magnitude, are relatively sensitive points of intensity according to the variance of the voltage applied to modulator 5. As shown in the figure, it is clearly seen that at no applied modulator voltage curve 23 is in the phase insensitive region. Moreover plots 21 and 25 represent a higher degree of phase sensitivity than plots 22 and 24. It is also significant that plots 21 and 22 show phase sensitivity in the opposite direction to that shown in plots 24 and 25. It is therefore shown that by regulating the voltage applied to modulator 5 the sensitivity of the intensity detected at photodetector 11 to the surface reflectance of object 9 can be minimized or maximized Dimensional measurements are taken with the sensitivity to reflectivity minimized and the sensitivity to phase difference maximized.

FIG. 3 shows plots of the intensity detected when the beams are scanned across the same set of grooves in a disk. Plots 31 through 35 were generated at different applied modulator voltages. It can be seen that the intensity detected depends on the degree of phase sensitivity selected via the applied modulator voltage. It should, thus, be obvious to conclude that the intensity can be made phase sensitive or phase insensitive by selecting the appropriate interferometer conditions.

By operating the interferometer in the phase insensitive mode, defects on the surface of object 9 may be detected. In this mode, the phase of the reflected beams is not a function of the depth or step height; the intensity of the beams is a function of the reflectivity of the surface of the object. Thus, a scratch or particulate matter on the surface of the object which causes a change in surface reflectivity, will show up as a change in the intensity detected by photodetector 11.

The technique embodied by this invention can be used to detect both dimensional measurements and defects on the fly in the manufacturing environment. That is, by altering the head voltage of modulator 5 electronically to switch modes, as opposed to rotating phase plate 10, which is a manual adjustment, the change between phase sensitive and phase insensitive modes can be done at rapid electronic speeds. To adjust the voltage applied to modulator 5, a regulated power supply is attached to modulator 5, which is programmable. A wafer or disk may be scanned by the interferometer while such is alternating back and forth between phase insensitive and phase sensitive modes. This permits characterization of both dimensional characteristics and defect detection across the wafer, disk, or any other type of object. When a defect is detected its size can be determined by continually scanning and observing when the intensity change that has been detected ceases.

While the invention has been particularly shown and described with reference to a preferred embodiment thereof, it will be understood by those skilled in the art that various changes in form and details may be made therein without departing from the spirit and scope of the invention. For example, energy beams other than light beams may be used. Also, the beams need not be orthogonally polarized, but merely of relatively different directions of polarization.

What is claimed is:

1. A method for making both dimensional measurements and defect detections on the surface of an object using a single interferometer, the interferometer including means for generating two discrete light beams incident upon different areas of the surface of the object and polarized in different directions, comprising:

adjusting the phase difference between the incident light beams such that the interferometer is phase sensitive and making dimensional measurements by observing the intensity of the light beams reflected from the object; and adjusting the phase difference between the incident light beams such that the interferometer is phase insensitive and detecting defects by observing the intensity of the light beams reflected from the object.

2. The method of claim 1, further comprising scanning the incident light beams across the surface of the object and repeating the steps of adjusting the phase difference between the incident light beams such that the interferometer is in phase sensitive and phase insensitive modes respectively.

3. A method for making both dimensional measurements and defect detections on an object using a single interferometer, the interferometer including means for generating two discrete light beams incident upon different areas of the surface of the object and polarized in different directions and a phase modulator having a voltage applied thereto which is determinative of the phase difference between the incident light beams, comprising:

adjusting the voltage applied to the phase modulator such that the intensity of the light beams reflected from the object is relatively sensitive to the incremental phase difference imparted to the light beams by the surface topography of the object and making dimensional measurements by observing the intensity of the light beams reflected from the object; and adjusting the voltage applied to the phase modulator such that the intensity of the light beams reflected from the object is relatively insensitive to the incremental phase difference imparted to the light beams by the surface topography of the object and detecting defects by observing the intensity of the light beams reflected from the object.

4. The method of claim 3, further comprising scanning the incident light beams across the surface of the object and repeating the steps of adjusting the voltage applied to the phase modulator such that the interferometer is in phase sensitive and phase insensitive modes respectively.

5. An interferometric method for making both dimensional measurements and defect detections on an object, comprising:

generating two discrete light beams incident upon different areas of the surface of the object and polarized in different directions;

adjusting the phase difference between the incident light beams such that the intensity of the light beams reflected from the object is relatively sensitive to the incremental phase difference imparted to the light beams by the surface topography of the object;

making dimensional measurements by observing the intensity of the light beams reflected from the object;

adjusting the phase difference between the incident light beams such that the intensity of the light beams reflected from the object is relatively insensitive to the incremental phase difference imparted to the light beams by the surface topography of the object; and detecting defects by observing the intensity of the light beams reflected from the object.

6. The method of claim 5, further comprising scanning the incident light beams across the surface of the object and repeating the steps of claim 5.

* * * * *